(12) United States Patent  (10) Patent No.: US 8,187,300 B2
Funamura  (45) Date of Patent: May 29, 2012

(54) ORGANOPEXY TOOL AND ORGANOPEXY KIT

(75) Inventor: Shigeaki Funamura, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 810 days.

(21) Appl. No.: 12/298,828

(22) PCT Filed: Apr. 28, 2006

(86) PCT No.: PCT/EP2006/004040
§ 371 (c)(1),
(2), (4) Date: Oct. 28, 2008

(87) PCT Pub. No.: WO2007/124772
PCT Pub. Date: Nov. 8, 2007

(65) Prior Publication Data
US 2009/0198256 A1 Aug. 6, 2009

(51) Int. Cl.
A61B 17/04 (2006.01)
(52) U.S. Cl. ......... 606/232; 606/139; 606/144; 600/201
(58) Field of Classification Search .................. 606/139, 606/144–148, 151, 213, 220, 232; 411/341, 411/344; 600/201
See application file for complete search history.

(56) References Cited

U.S. PATENT DOCUMENTS

| 3,749,086 A | 7/1973 | Kline et al. |
| 3,835,863 A | 9/1974 | Goldberg et al. |
| 4,077,412 A | 3/1978 | Moossun |
| 4,235,238 A * | 11/1980 | Ogiu et al. ............... 606/145 |
| 4,393,873 A | 7/1983 | Nawash et al. |
| 5,123,914 A * | 6/1992 | Cope ........................ 606/232 |
| 5,269,809 A * | 12/1993 | Hayhurst et al. ............ 606/232 |
| 5,702,352 A * | 12/1997 | Kimura et al. ............ 600/201 |
| 6,068,648 A | 5/2000 | Cole et al. |
| 7,850,712 B2 * | 12/2010 | Conlon et al. ............. 606/232 |
| 7,875,056 B2 * | 1/2011 | Jervis et al. .............. 606/232 |
| 7,905,889 B2 * | 3/2011 | Catanese et al. ........... 606/139 |
| 2001/0021855 A1 * | 9/2001 | Levinson ................... 606/144 |
| 2003/0191497 A1 * | 10/2003 | Cope ........................ 606/215 |

FOREIGN PATENT DOCUMENTS

EP 0 246 836 A2 11/1987
(Continued)

OTHER PUBLICATIONS

PCT/EP2006/004040 International Search Report (Last two pages), dated Jan. 2, 2007.

Primary Examiner — Corrine M McDermott
Assistant Examiner — Mark Mashack
(74) Attorney, Agent, or Firm — Elias Domingo, Esq.

(57) ABSTRACT

The present invention provides an organopexy tool (10, 40) comprising a locking part (11, 41) and suture thread (12, 42). Locking part (11, 41) is made of a rod-shaped part (13, 14), and the coil spring (14) that covers the rod-shaped part (13, 43) and is affixed to one end (13a, 43a) of rod-shaped part (13, 43), and suture thread (12, 42) is connected to the middle of rod-shaped part (13, 43) through the inside of coil spring (14) from one end (13b, 43b) of rod-shaped part (13, 43). Insertion tool (20, 50) has a puncture needle (21) for insertion that can house the locking part (11, 41) and a tubular push-out part (22) that is inserted into puncture needle (21) to push locking part (11, 41) out of the tip (25).

9 Claims, 20 Drawing Sheets

FOREIGN PATENT DOCUMENTS

| | | |
|---|---|---|
| JP | 63-023651 | 1/1988 |
| JP | 04-226643 | 8/1992 |
| JP | 04-231946 | 8/1992 |
| JP | 05-161655 | 6/1993 |
| JP | 08-150149 | 6/1996 |
| JP | 2005-525137 | 8/2005 |
| JP | 2006-296796 | 11/2006 |
| WO | WO 2006/037639 A | 4/2006 |

* cited by examiner

ORGANOPEXY TOOL AND ORGANOPEXY KIT

TECHNICAL FIELD

The present invention relates to an organopexy tool and to an organopexy tool set used for affixing a prescribed organ in a patient's body to a body wall, and in particular the organopexy tool has an elastic telescoping member for inserting and removing suturing thread from a hole made in a patient.

PRIOR ART

In the prior art, as cited in Japanese Kokai Patent Application Number HEI 5[1993]-161655, organopexy tool sets are provided with an organopexy tool for affixing a sutured part, a body wall and an internal organ. For example, for a patient refusing to ingest food or unable to do so, a gastric tube would be used to introduce nutrient and fluid into the patient. This is done by forming a hole in a patient's stomach and inserting a gastric feeding tube, as disclosed in Meier U.S. Pat. No. 6,458,106 and also owned by the assignee of the present application. In order to properly attach the molded gastric tube, the abdominal wall and the gastric wall would be affixed beforehand using an organopexy tool kit provided with an organopexy tool (cf. HEI 5[1993]-161655).

In the prior art organopexy tool set, the set has two puncture needles used in parallel, one slidable inside the other, to affix the abdominal wall and gastric wall at the point of suture for the patient. After insertion of the needles, a suture thread is passed into and through the internal or inner puncture needle, and a loop composed of wire at the tip is passed into the internal needle. The internal needle is pulled from the puncture needle with the suture thread held in the loop on the inside of the gastric wall. Then, after the end part of the suture thread is pulled up from the other puncture needle, the two puncture needles are pulled out of the sutured part. The abdominal wall and gastric wall is fixed when the two ends of the protruding suture thread are tied together.

SUMMARY OF THE INVENTION

However, with the conventional organopexy tool set described in patent reference, the two puncture needles are inserted simultaneously, and an internal needle and its suture thread must be passed through the puncture needle or outer needle for insertion. This operation is cumbersome and difficult. Also, if the internal needle is not properly inserted into the puncture needle, the protrusion direction or shape of the loop will not be correct, and the suture thread will not be caught. Consequently, much skill is required by the practitioner. Also, because there is insufficient space on the inside of the sutured part, it is difficult to catch and hold the suture thread with the loop, resulting in poor operating reliability.

The purpose of the present invention is to solve the aforementioned problems of the prior art by providing an organopexy tool and organopexy tool set that can affix an organ in a simple operation with high reliability.

In order to realize the above objective, the present invention is composed of an organopexy tool comprising a locking part and a suture thread that is connected to the locking part, the locking part is disposed on the inner wall of the affixed organ, with the suture thread attached approximately halfway along the axial surface of the locking part, for affixing an organ to a body wall. The body wall is a wall of a body cavity or a like position on the dermal side and the body wall excludes internal organ walls.

The suture thread is passed through a hole formed in the patient's organ and the body wall and the thread extends outside the patient's body. The locking part comprises a rod-shaped part and an elastic telescoping member that is fixed to first end or end portion of the rod-shaped part and the telescoping member covers the outer peripheral surface, along the axial direction, of the rod-shaped part. The other end of the elastic telescoping member is positioned at the start of the exposed part of the suture thread, of the rod-shaped part. The suture thread is exposed and attached at a mid-point along the rod-shaped part, and extends outside the other end of the elastic telescoping member. The practitioner pulls the suture thread from the portion at the other end of the rod-shaped part. The pulling force causes the elastic telescoping member to contract, and when the pulling force is released, the elastic telescoping member extends to substantially its original length.

The organopexy tool consists of a rod-shaped locking part disposed on the inner wall of the organ and a suture thread that is external to the patient through a hole. The rod-shaped locking part is composed of a rod-shaped part and an elastic telescoping member that is affixed to a portion at one end of the rod-shaped part. The elastic telescoping member covers part of the outer peripheral surface of the rod-shaped part. The end part of the suture thread extends from approximately a mid-point of the rod-shaped part, to the other end of the rod-shaped, then through the hole to the outside of the patient. The suture thread is positioned between the telescoping elastic member and the outer periphery of the rod-shaped part. The rod-shaped locking part can be oval, squared or another shape, as long as the part slides within the puncture needle.

The approximate middle part or the mid-point is the point of attaching the suture thread to the rod-shaped part to form a T shape when the suture thread is pulled from outside the patient's body to position the locking part against the inner wall. One end of the rod-shaped part refers to one end, one end side refers to the direction of the one end, and portion at one end refers to a prescribed portion positioned near the end including the one end. In the same way, the other end of the rod-shaped part refers to the end in the opposite direction from the one end, the other end side refers to the direction of the end opposite from the one end, and portion at the other end refers to a prescribed portion positioned near the end including the end opposite the one end.

When inserting the organopexy tool, the elastic telescoping member is extended. This positions the locking part and the suture part in an axial orientation with the inner cannula of the puncture needle. The practitioner positions the locking part inside the organ, using the insertion tool and then the suture thread is pulled positioning the locking part against the inner wall of the organ. The pulling of the thread affixes the organ wall to the body wall by the locking part and the suture thread forming a T shape.

When removing the organopexy tool, the elastic telescoping member expands by releasing the force pulling the suture thread against the locking part, and the locking part and the suture thread are put into a straight line. This allows the locking part to be removed from the hole easily. The end of the suture thread is connected to the mid-point of the rod-shaped part by a hole therethrough.

The rod-shaped part in this case is in particular a columnar rod shape, or a tubular rod shape. The end of the suture thread may also be connected by caulking, adhesive, or a screwed. The end of the suture thread may be connected to another portion of the rod-shaped part and be outside of the elastic telescoping member.

In yet another characteristic feature of the organopexy tool, the rod-shaped part of the locking part comprises a cylindrical body and a notch part that is through the inner peripheral surface of the tubular body to the outer peripheral surface through which the suture thread can pass from the approximate middle part, axially to the tubular body to the other end. Because of this, when the elastic telescoping member is extended and the locking part and the suture thread are in a straight line, the suture thread is housed inside the rod-shaped part, so the suture thread is secured. In a case when the elastic telescoping member is a linear member, e.g., a coil spring, the coil spring helps to prevent tangling between the elastic telescoping member and the suture thread.

In yet another characteristic feature of the organopexy tool, an engaging part is furnished at the end of the suture thread and the suture thread is suitable to be passed through the inside of the portion at one end of the rod-shaped member and extended to the outside from the notch part or the open part at the other end with the engaging part engaged at the open edge at one end of the rod-shaped part constituted with a cylindrical body. This improves the reliability of the locking part and the suture thread. The engaging part is not limited provided the engaging part can fit into the open end of a rod-shaped part constituted with a sphere, a rod-shaped body, a sheet-like body, frame body or other cylindrical body and connected with the suture thread. The engaging part is suitable to be formed by connecting the end of the suture to form it into a mass. With this, a separate member to constitute the engaging part is not necessary.

In yet another characteristic feature of the organopexy tool, the organopexy tool set is provided with an organopexy tool and an insertion tool. The insertion tool comprises a member used to discharge the locking part after being inserted into the patient's body. The insertion tool applies the force necessary to bring the suture thread away from the portion at the other end of the rod-shaped part. The insertion tool comprises a needle that is suitable to be inserted into the patient's body by puncturing, or it is suitable to be made of a tubular body, the tip of which is not sharp, that is suitable to be inserted into a hole formed in the patient's body beforehand. The suture thread is suitable to be passed through the inside of the insertion tool, or it is suitable to follow the outer peripheral surface of the insertion tool. This facilitates the attaching the organopexy tool to the organ.

In yet another characteristic feature of the organopexy tool, the insertion tool comprises a puncture needle for insertion that is suitable to house or contain the locking part and a tubular push-out part with the suture thread threaded inside. The tubular push-out part is used to push the locking part housed, out from the opening at the tip of the puncture needle for insertion.

The combination of the suture thread inside the tubular push-out part as well as the puncture needle helps with the inserting the insertion tool into the patient's body. The locking part is wider than the suture thread passing through the hole in the patient and through the puncture needle for insertion, improving the operation for forming the suture thread and the locking part into a T shape. The tubular push-out part pushes the locking part out of the puncture needle. The portion of the suture thread at the end of the rod-shaped part is suitable to be separated therefrom while the elastic telescoping member is contracted, by pulling the base end portion (portion protruding outside) of the suture thread with the tubular push-out part against the locking part. In this case, the tip of the tubular push-out part is suitable to be formed into a tapered shape so that the tips of the tubular push-out part can enter the gap between the suture thread and the rod-shaped part of the locking part. Because of this, when the base end portion of the suture thread is pulled after the locking part is pushed out of the puncture needle, the locking part will open in a direction perpendicular to the suture thread.

In yet another characteristic feature of the organopexy tool, the organopexy tool set is provided with an organopexy tool and a removal tool to remove the organopexy tool from inside the patient. The removal tool comprises a tubular body in which the suture thread and the locking body is suitable to be inserted, and the suture thread is inserted into a hole in the patient while housed inside the removal tool. The locking part is separated from the inner wall of the organ, and the elastic telescoping member is extended, and then the locking part and the suture thread are placed in a straight line, and then the locking part is suitable to be housed inside the removal tool by pulling the base end portion of the suture thread.

The removal tool makes the removal of the organopexy tool less cumbersome. Inserting the removal tool, with the suture thread passing inside the removal tool, and by pushing the locking part, the locking part is suitable to be removed from the inner wall of the organ. The insertion of the removal tool releases the force (for example the telescoping elastic member) pressing the suture thread against the rod-shaped body of the locking part, and the elastic telescoping member extends. The release of force causes the locking part and the suture thread to be placed into a straight line by the extension of the elastic telescoping member, and then the locking part is suitable to be housed in the removal tool and removed through the hole in the patient.

In yet another characteristic feature of the organopexy tool, the removal tool comprises a cylindrical part and a grip part located at the base end of the cylindrical part, and a spiral-shaped notch part that extends axially while encircling the periphery from the tip of the cylindrical part to the base end portion passing between the outer peripheral surface and the inner peripheral surface of the cylindrical part. This allows the user to insert the removal tool in the hole in the patient and during insertion rotate to place the suture thread into the notch part. The rotation, in part, allows the user to place the locking part and the suture thread into a straight line, housed in the removal tool, and then remove the organopexy tool from the patient's body.

BRIEF DESCRIPTION OF THE FIGURES

Preferred embodiments of the invention will now be described, by way of example only, with reference to the accompanying drawings in which.

DETAILED DESCRIPTION OF PREFERRED EMBODIMENTS OF THE INVENTION

Figure 1:
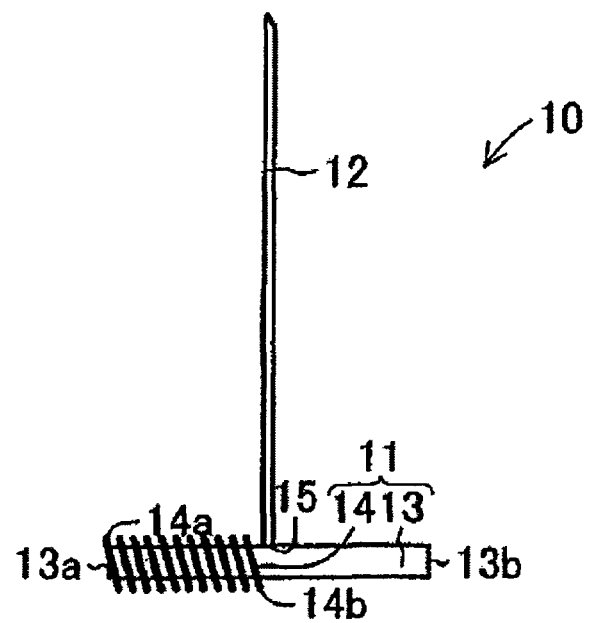
FIG. 1 is a front view showing an organopexy tool pertaining to a first embodiment of the present invention when affixed.
Figure 2:
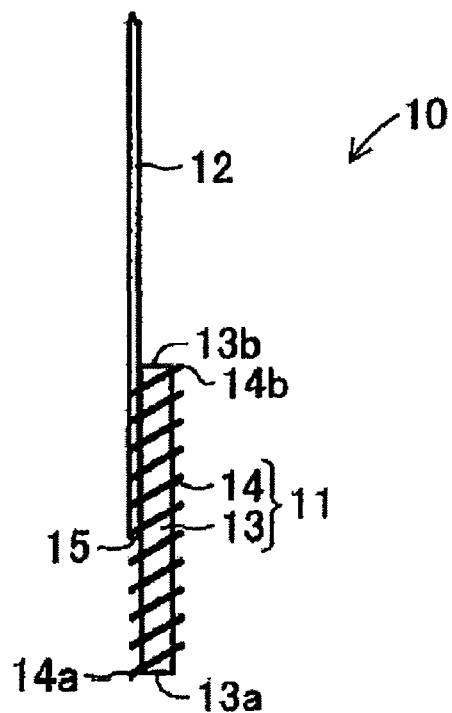
FIG. 2 is a front view showing an organopexy tool when the coil spring is extended and the locking part and the suture thread are extended in a straight line.

FIGS. 1 and 2 illustrate the organ fixing tool (10) of this embodiment. Organopexy tool (10) is used to suture abdominal wall (A), which is the patient's body wall, and gastric wall (B) (refer to FIG. 5), for example. The organopexy tool is composed of a locking part (11) formed in a rod shape and a suture thread (12) connected to the center part, in the axial orientation, of locking part (11). Locking part (11) is a rod-shaped part (13) composed of a round columnar body made out of stainless steel, and a coil spring (14) made of stainless steel is the elastic telescoping member that is attached to rod-shaped part (13) covering the outer peripheral surface of rod-shaped part (13).

As shown in FIG. 2, one end (14a) of coil spring (14) is affixed to one end (13a) of rod-shaped part (13). The other end (14b) will extend to other end (13b) of rod-shaped part (13). Having an end (14a) attached will allow the coil spring (14) to telescope axially along the rod-shaped part (13), with one end (14a) as the starting point. In this case, the tip (portion toward locking part (11)) of suture thread (12) passes between the portion at the other end (13b) of rod-shaped part (13) and the portion at the other end (14b) of coil spring (14) to extend outside.

As shown in FIG. 2, the portion at the end of suture thread (12) will follow the portion at the other end (13b) of rod-shaped part (13) by extending the coil spring (14), and the suture thread (12) and locking part (11) will be in a straight line. When a force is applied between locking part (11) and suture thread (12) to separate suture thread (12) from the portion at the other end (13b) of rod-shaped part (13), the coil spring (14) contracts toward the one end (13a) of rod-shaped part (13) thus allowing the locking part (11) and suture thread (12) to meet at a right angle to form a T shape, as shown in FIG. 1. The coil spring (14) telescopes while moving the other end (14b) between connection part (15) and the other end (13b) of rod-shaped part (13). Connection part (15) constitutes the part where exposure starts of the suture thread (12) and the rod-shaped part (13). The suture thread (12) is made of nylon.

Figure 3:
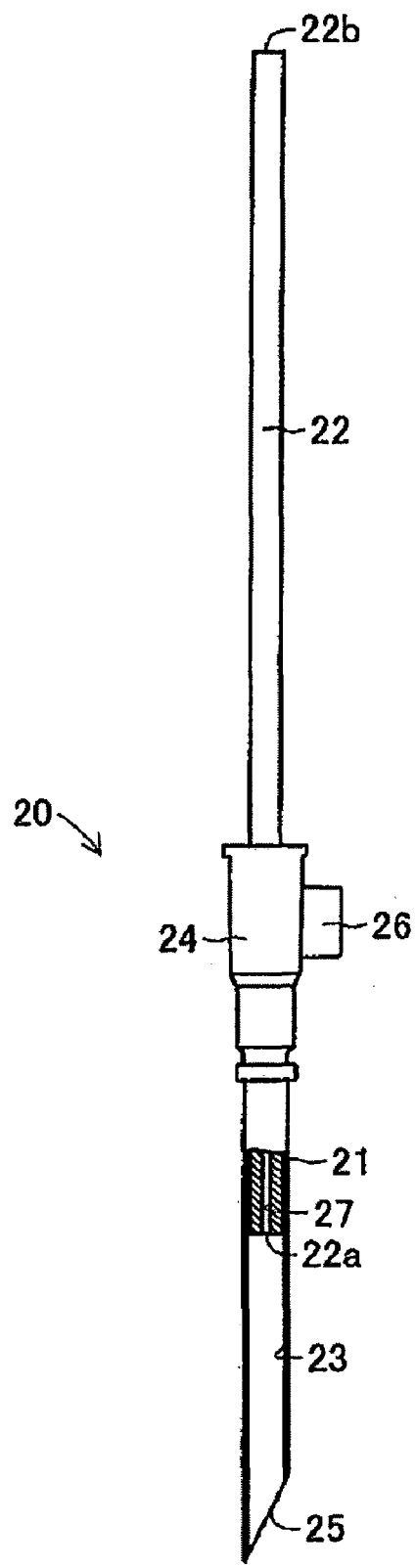
FIG. 3 is a partial cutaway cross section showing the insertion tool.

FIG. 3 illustrates the insertion tool (20) for attaching the organopexy tool (10) to the abdomen of the patient. Insertion tool (20) is constituted with puncture needle (21) for insertion and tubular push-out part (22) that is inserted into the puncture needle (21). Puncture needle (21) is composed of a cylindrical body made of stainless steel inside from which an insertion hole (23) is formed the inside of the puncture needle (21), and a grip part (24) is formed at the base end (top end in FIG. 3). Grip part (24) is formed into a tubular shape, the upper part of which is large in diameter and the lower part of which is small in diameter, and a guide hole (not shown) that connects to insertion hole (23) is formed inside.

Figure 4:
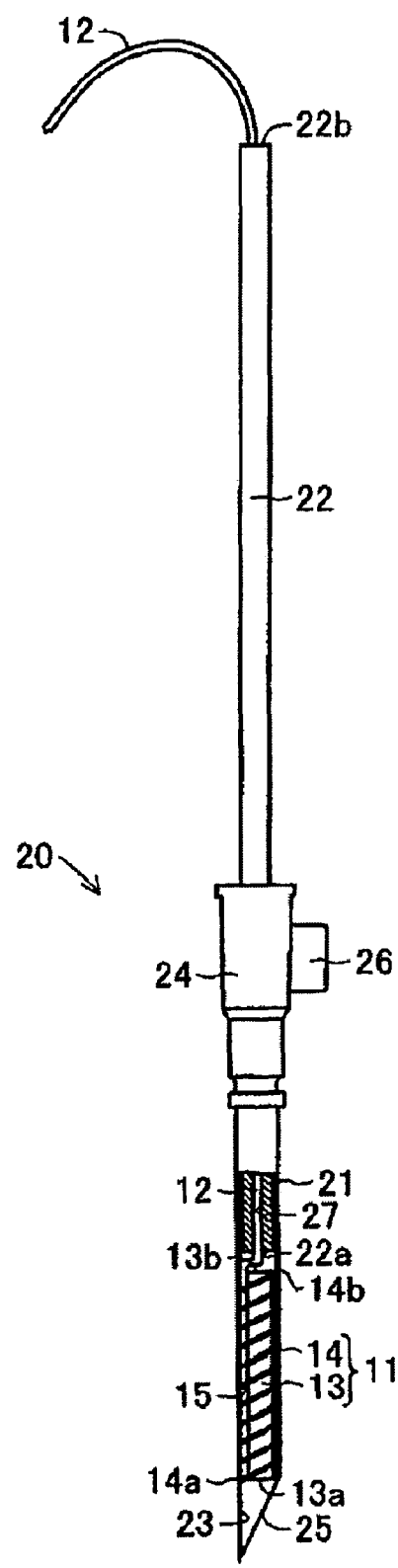
FIG. 4 is a partial cutaway cross section showing the organopexy tool attached to the insertion tool shown in FIG. 3.

The diameter of the guide hole (not shown) is set to be larger than the diameter of insertion hole (23), and because of this, it is easy to insert tubular push-out part (22) from the upper end of the puncture needle (21) for insertion. The diameter of the insertion hole (23) is set to a size at which locking part (11) and suture thread (12) of organopexy tool (10) suitable to be inserted together in a straight line as shown in FIG. 2 and FIG. 4. The tip (25) of puncture needle (21) is cut diagonally relative to the axial orientation, giving a point, and is formed so that the open part faces horizontally.

Referring to FIG. 3, a projection (26) is formed axially on the outer peripheral surface of grip part (24). The opening direction of tip (25) of puncture needle (21) is identified by projection (26). Tubular push-out part (22) comprises a cylindrical body made of stainless steel inside of which insertion hole (27) is formed. The outer diameter of tubular push-out part (22) is set to a size at which it can be inserted inside insertion hole (23) of puncture needle for insertion (21), and the inner diameter of insertion hole (27) is set to a size through which suture thread (12) suitable to pass and through which locking part (11) will not pass.

Referring to FIG. 4, upon attaching the organopexy tool (10) to the insertion tool (20), the locking part (11) is pointed vertically inside insertion hole or opening (23) of puncture needle (21), then the tubular push-out part (22) is inserted at the upper end of insertion hole (23). The suture thread (12) is caused to follow the portion at the other end (13b) of rod-shaped part (13), and one end (13a) is positioned downward and the other end (13b) upward with locking part (11) and suture thread (12) put into the straight line, also shown in FIG. 2. Next, the portion at the base end of suture thread (12) protruding from the upper end of grip part (24) is inserted into insertion hole (27) through the tip opening (22b) in tubular push-out part (22) and caused to protrude outside of the upper end opening.

As shown in FIG. 4, the organopexy tool (10) and tubular push-out part (22) are inserted from the upper end of the guide hole in grip part (24) and enter the puncture needle (21). The base end of suture thread (12) is pulled lightly so that suture thread (12) is not slack. The tubular push-out part (22) is moved toward tip (25) of puncture needle (21) while pushing locking part (11) with the tip (22a) of tubular push-out part (22), and insertion of tubular push-out part (22) is stopped at the point when the lower end of locking part (11) (one end (13a) of rod-shaped part (13)) is positioned near the lower end of insertion hole (23).

Figure 5:
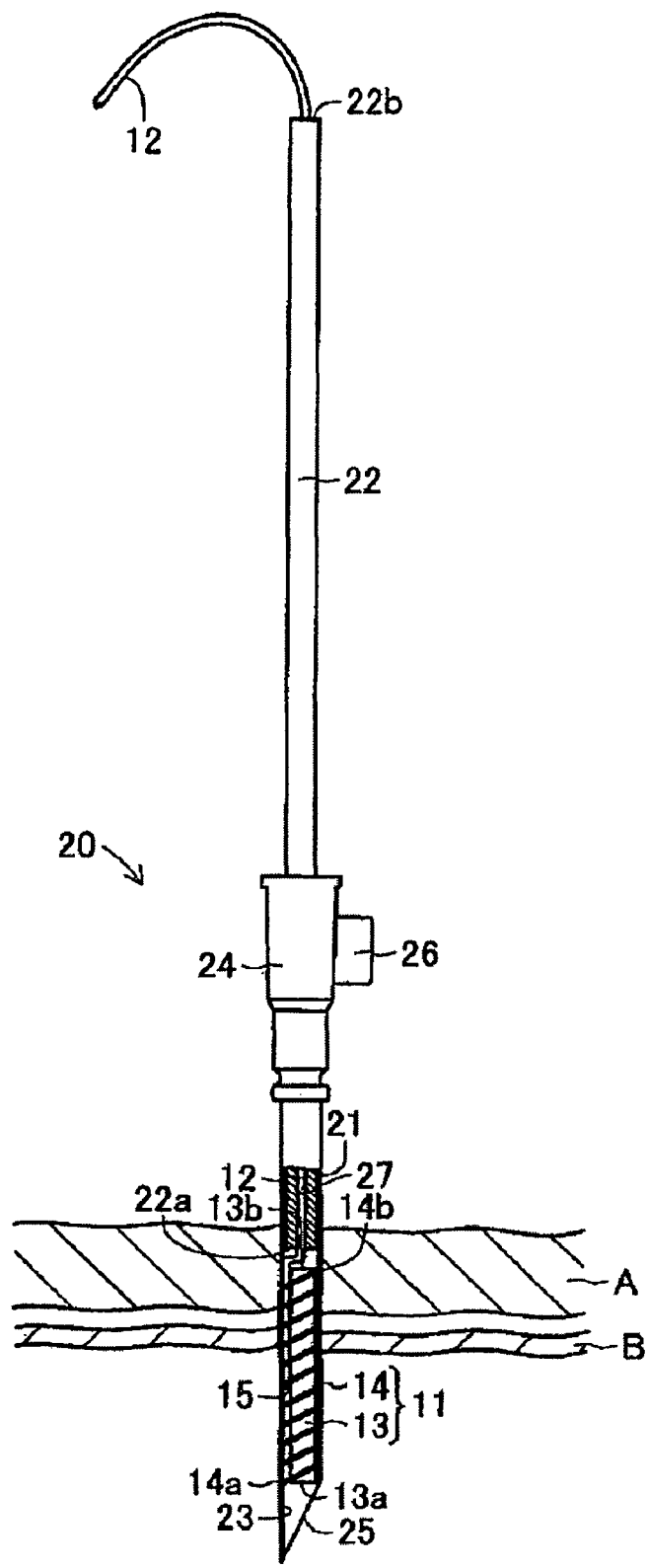
FIG. 5 is a cross section showing the insertion tool shown in FIG. 4 puncturing the abdomen.
Figure 6:
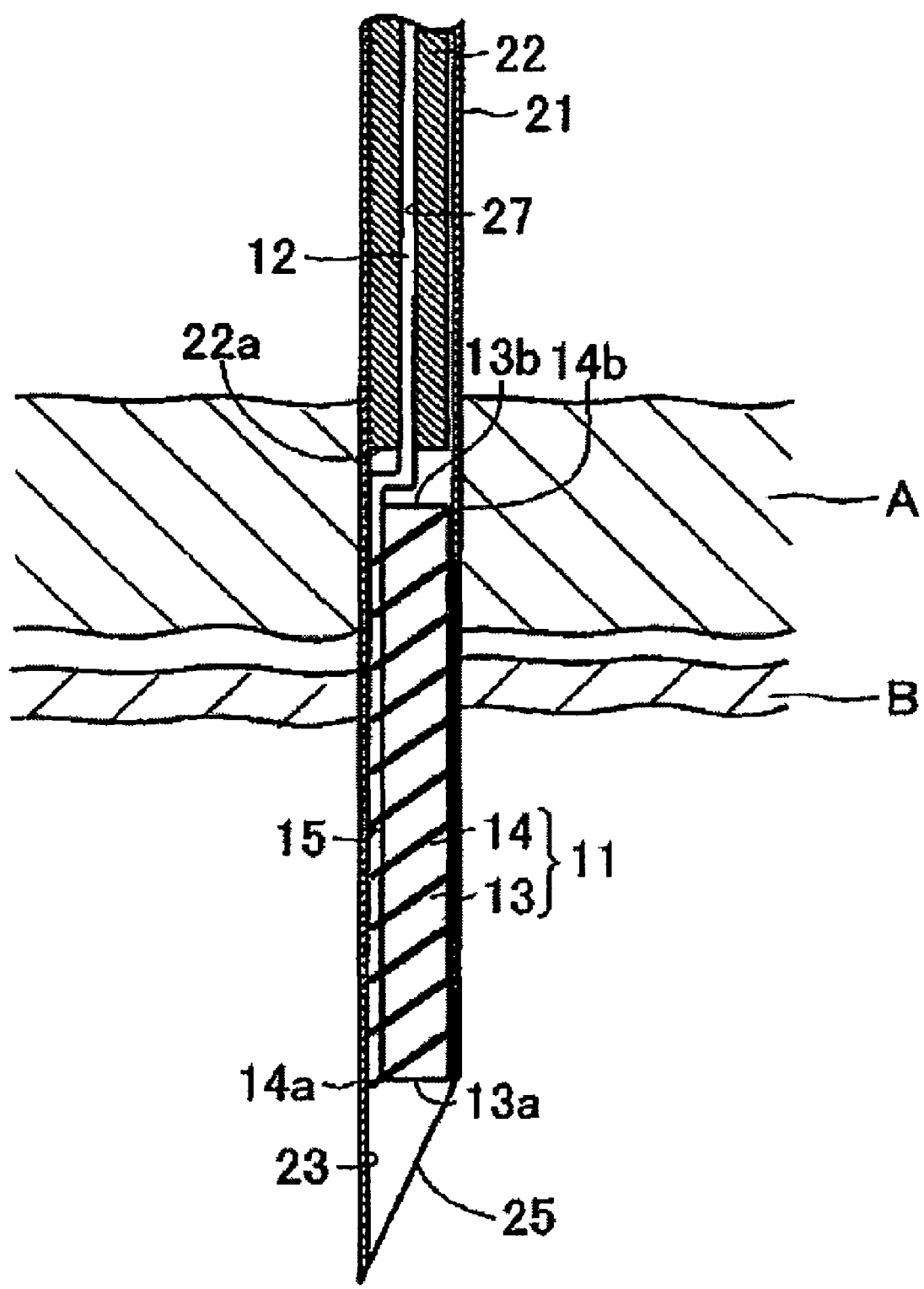
FIG. 6 is a cross section showing the major parts in FIG. 5 enlarged.
Figure 7:
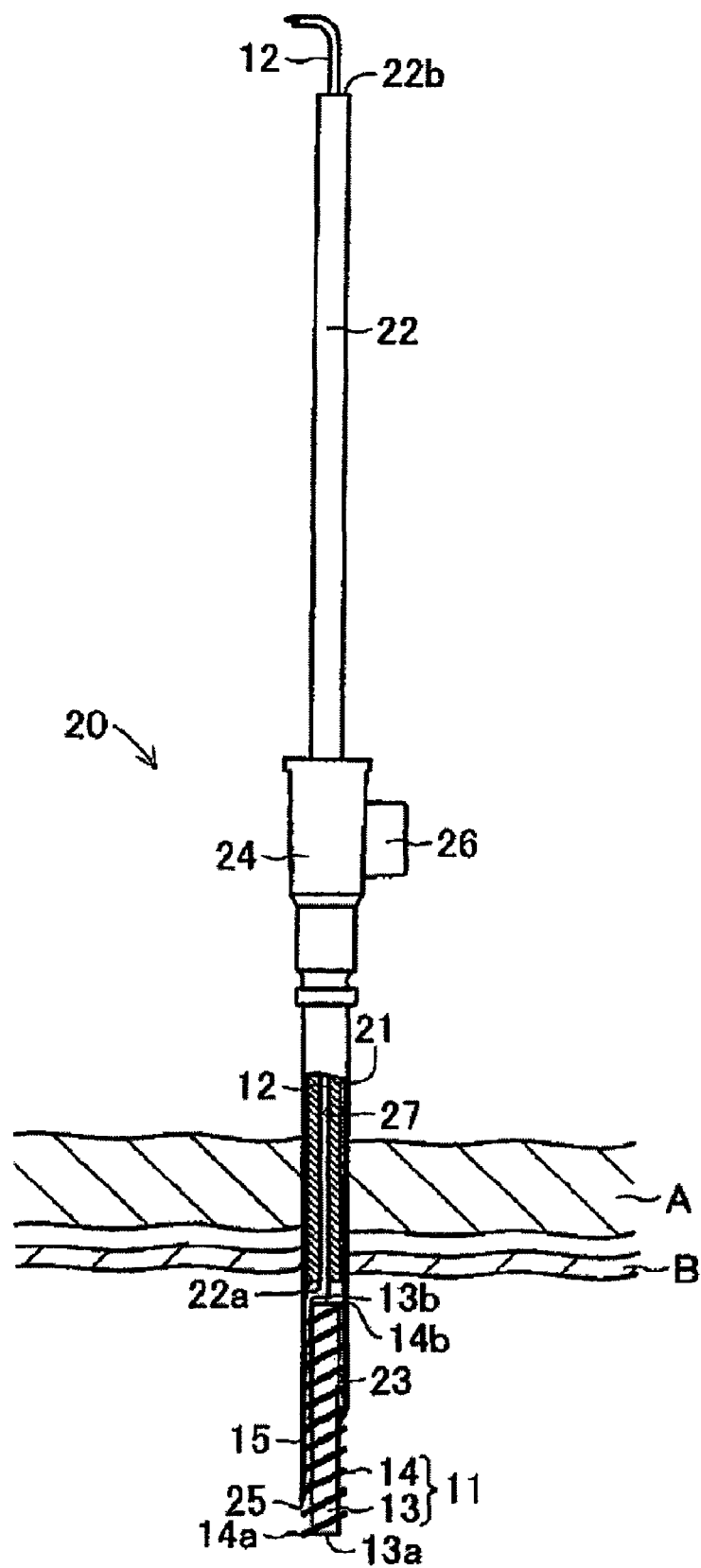
FIG. 7 is a partial cutaway cross section showing the locking part inserted inside the gastric wall.
Figure 8:
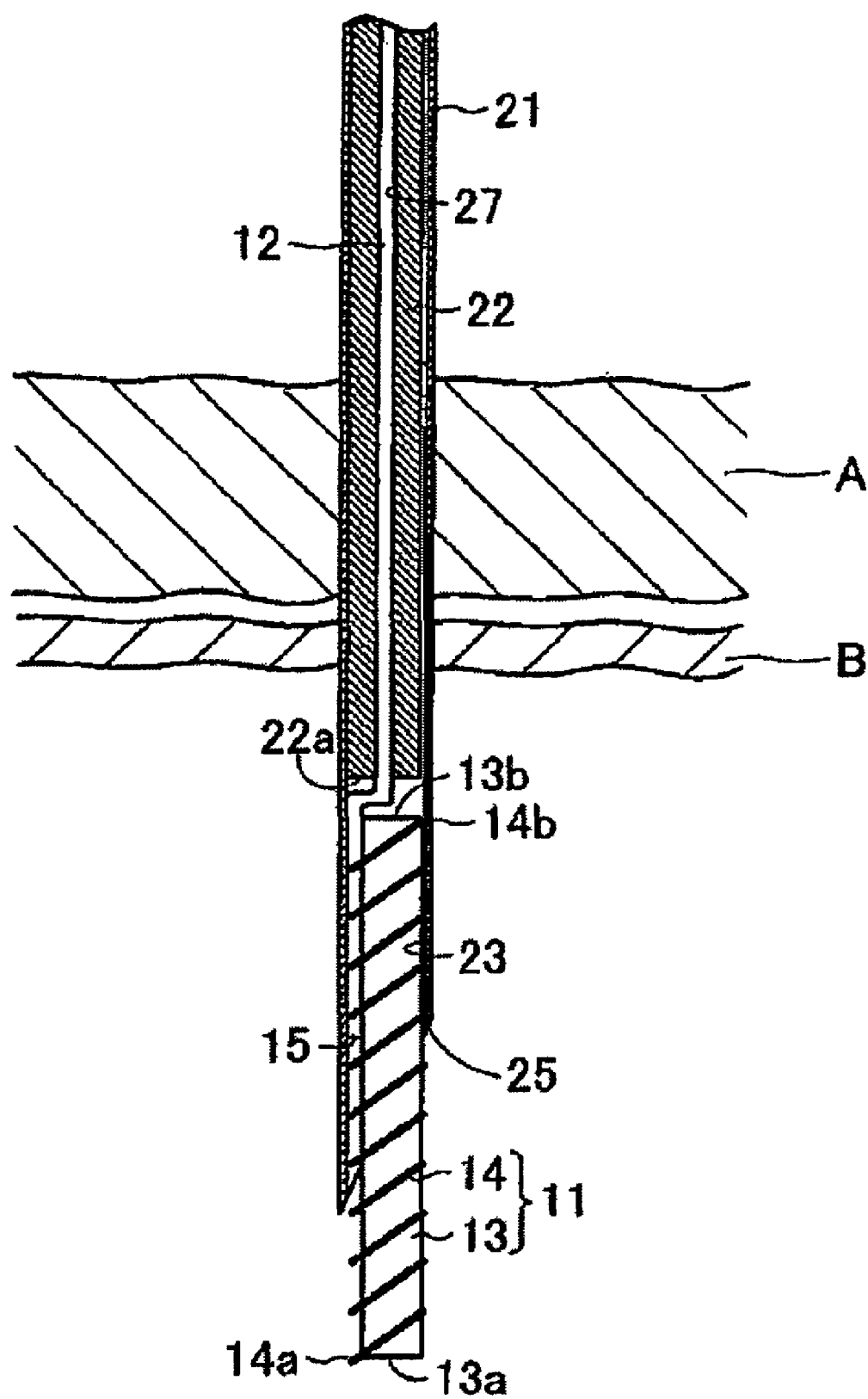
FIG. 8 is a cross section showing the major parts in FIG. 7 enlarged.

As shown in FIG. 5 and FIG. 6, the puncture needle (21) pierces the abdominal wall (A) and the gastric wall (B). The insertion tool (20) is pushed through the skin surface until the opening in the tip (25) of puncture needle (21) is positioned on the inside of gastric wall (B). After insertion, the tubular push-out part (22) is inserted further into the lower part (inward side) of the puncture needle (21), as shown in FIGS. 7 and 8, until a part of locking part (11) protrudes from the tip (25) of the puncture needle (21).

Figure 9:
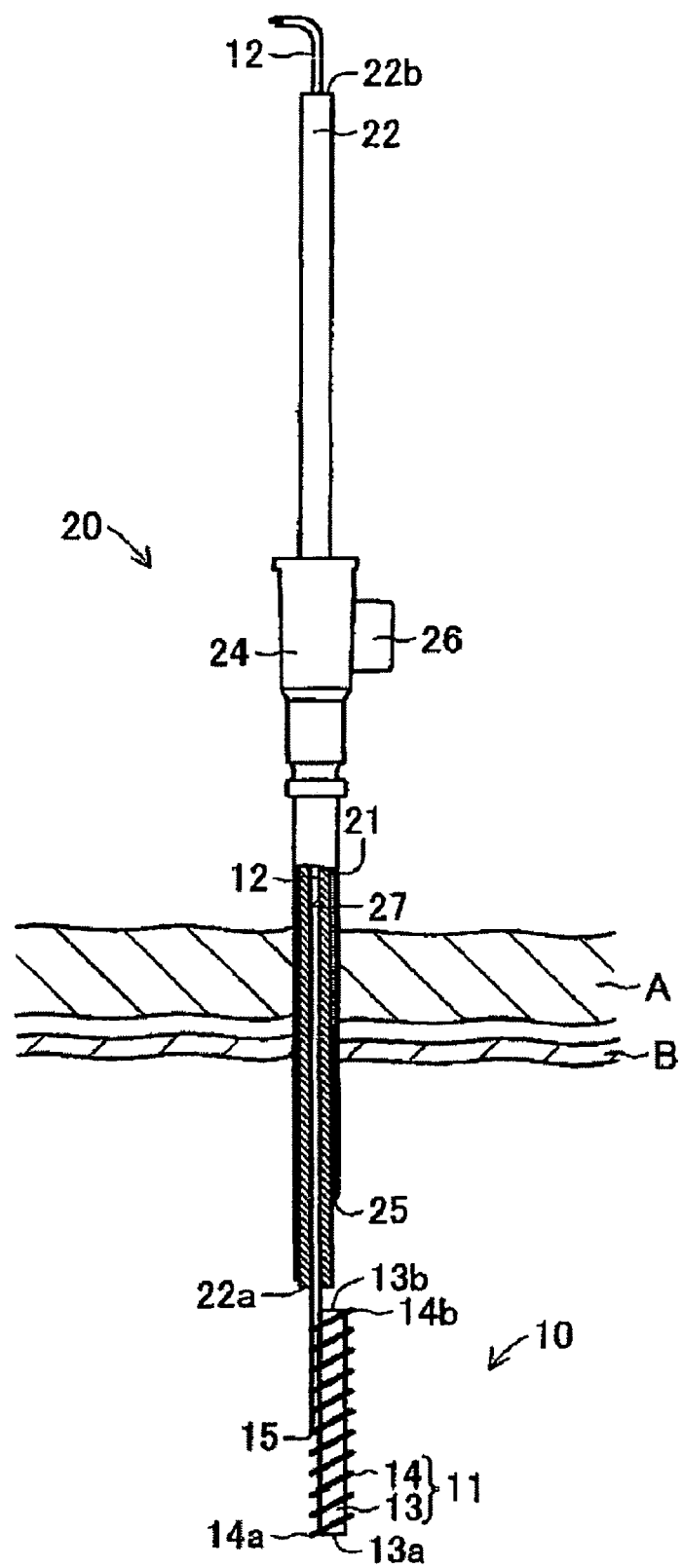
FIG. 9 is a partial cutaway cross section showing the locking part inserted inside the gastric wall.
Figure 10:
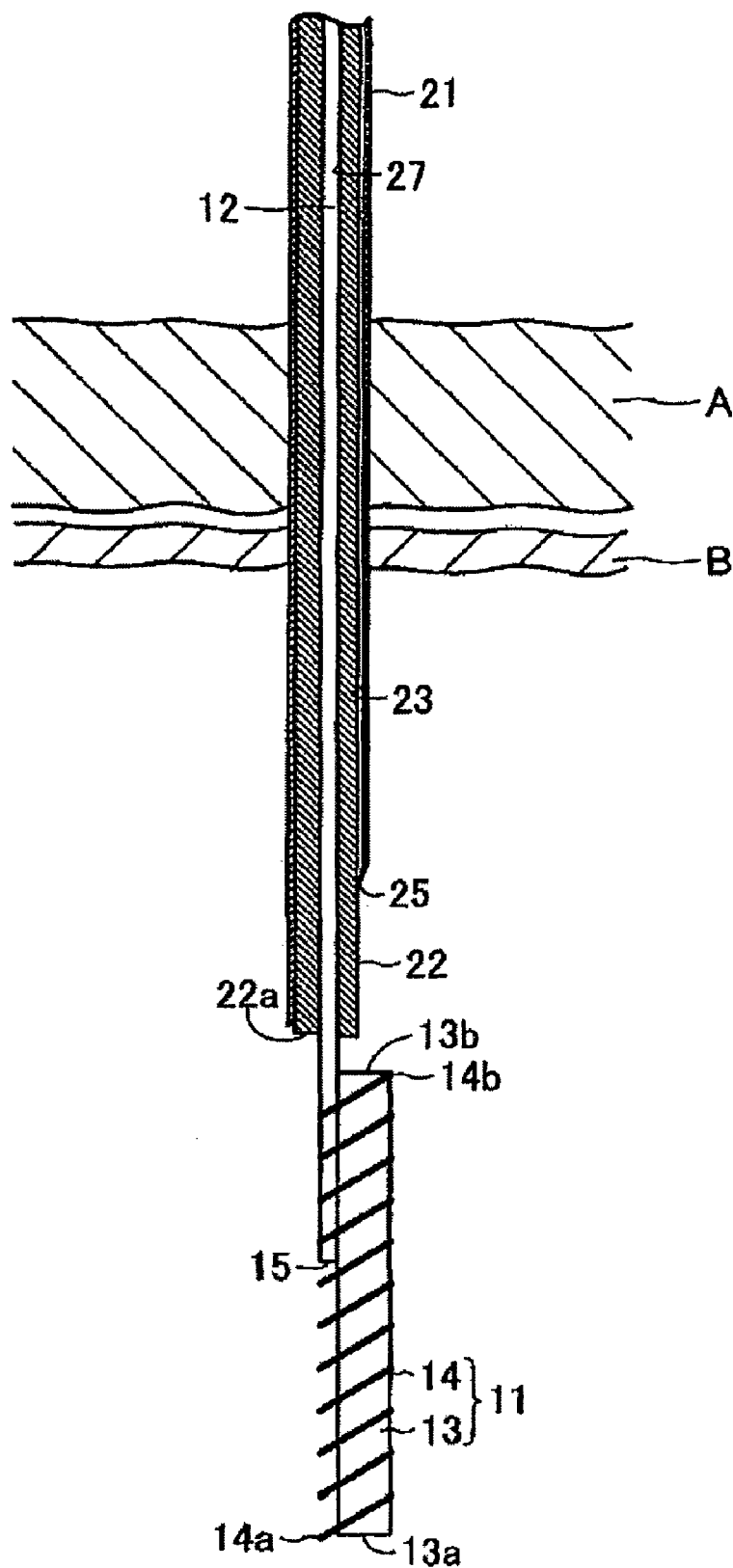
FIG. 10 is a cross section showing the major parts in FIG. 9 enlarged.
Figure 11:
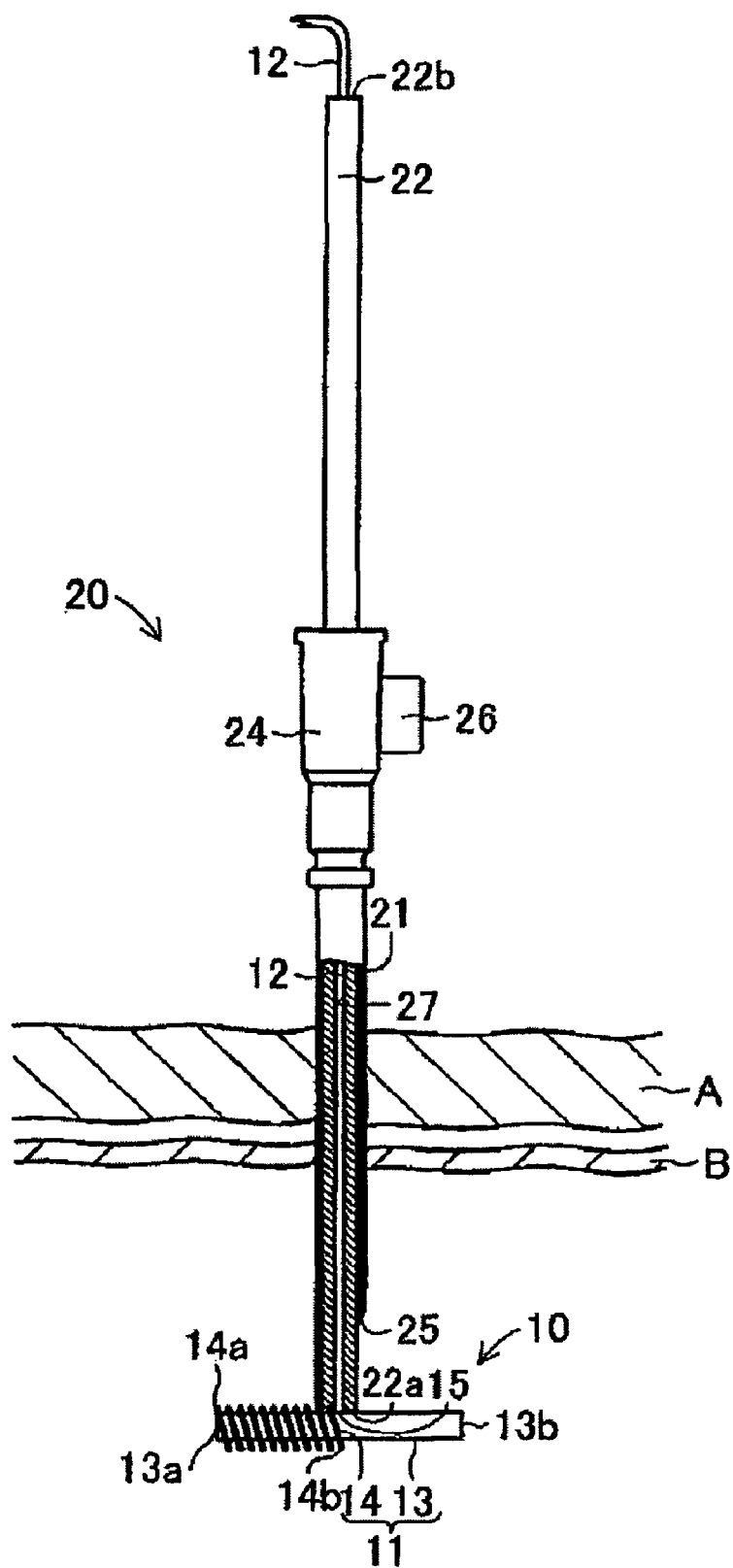
FIG. 11 is a partial cutaway cross section showing the suture thread pulled and the locking part and suture thread in a T shape.
Figure 12:
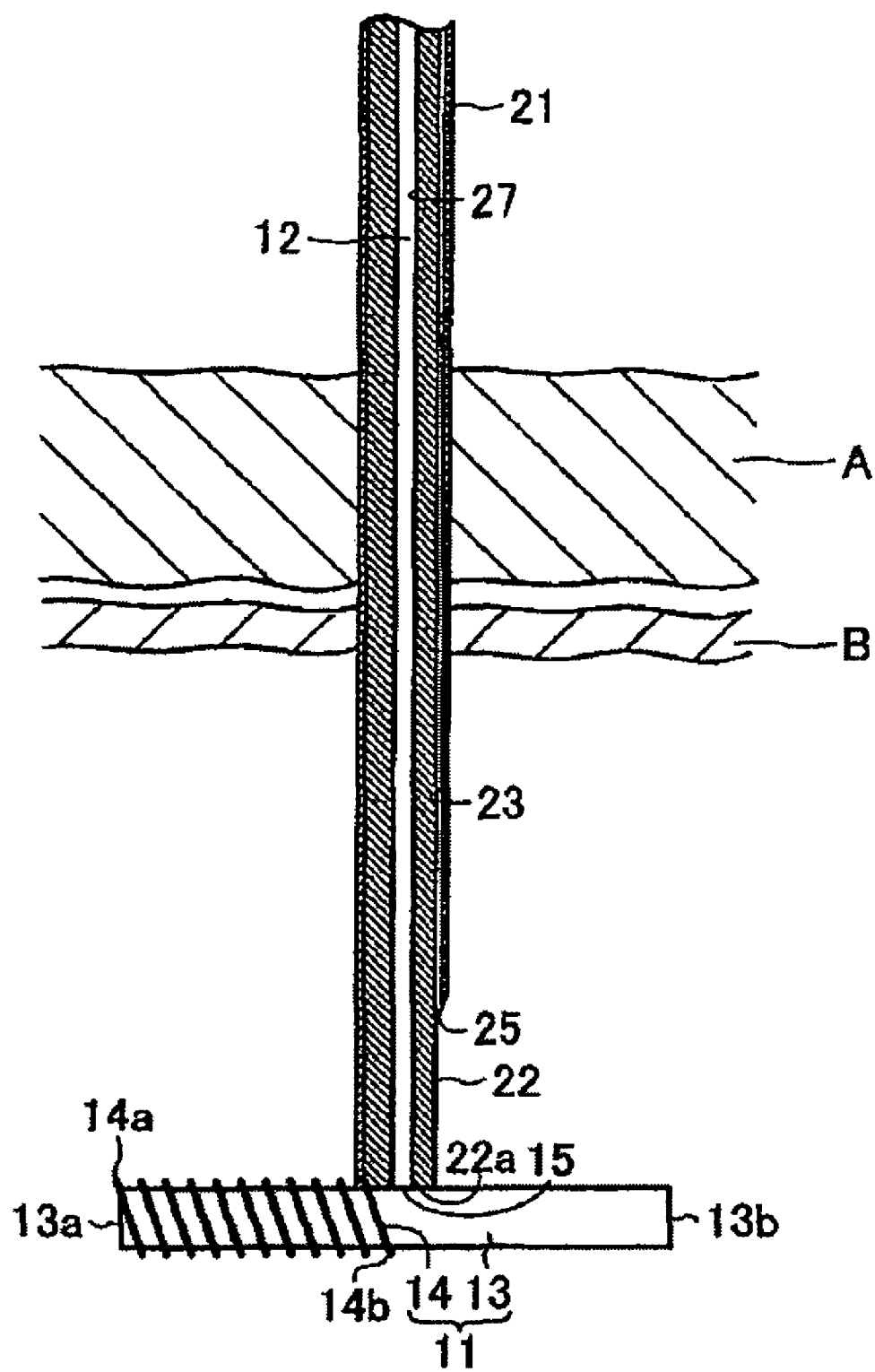
FIG. 12 is a cross section showing the major parts in FIG. 11 enlarged.

As shown in FIGS. 9 and 10, the tubular push-out part (22) is further inserted toward the lower part of puncture needle (21) until tip (22a) of tubular push-out part (22) protrudes from the tip (25) of puncture needle (21). Once locking part (11) is pushed outside of puncture needle (21) it is positioned on the inward side of gastric wall (B). Once positioned, the user pulls the portion at the base end of suture thread (12) (portion protruding from upper end (22b) of tubular push-out part (22)), as shown in FIGS. 11 and 12. In this case, tip (22a) of tubular push-out part (22) advances toward connection part (15) of suture thread (12) and rod-shaped part (13) while compressing coil spring (14) to force open the space between suture thread (12) and the other end (13b) of rod-shaped part (13) by suture thread (12) being pulled.

Figure 15:
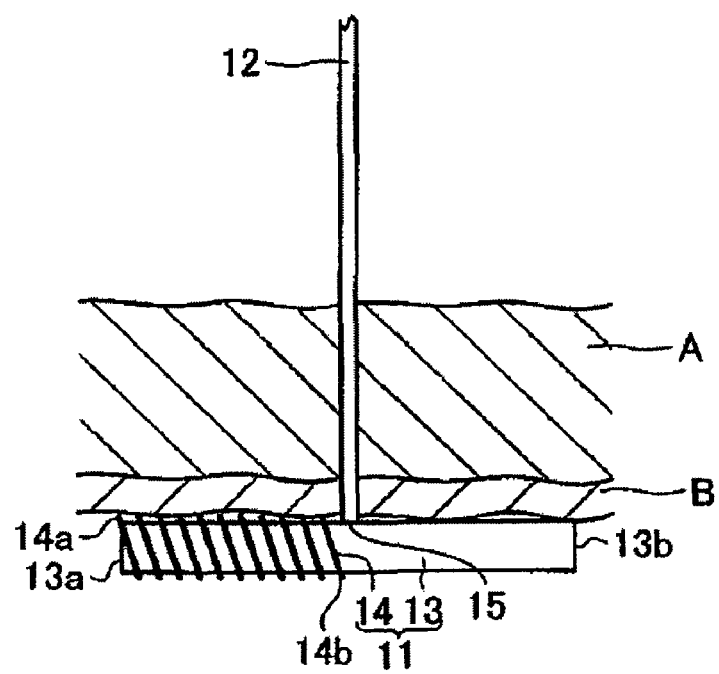
FIG. 15 is a cross section showing the insertion tool removed and the locking part engaged on the gastric wall.

As shown in FIGS. 11 and 12, advancing the tip (22a) to the connection (15) causes the locking part (11) and the suture thread (12) to form a T shape. In this state, locking part (11) is retracted until it touches gastric wall (B) in the direction of withdrawal of organopexy tool (10), and tip (25) of the puncture needle (21) is removed from gastric wall (B) and abdominal wall (A). As shown in FIG. 15, the puncture needle (21) is removed from tubular push-out part (22), and the organopexy tool (10) is left in the patient's body. The tubular push-out part (22) is removed from the patient's body. The locking part (11), as shown in FIG. 15, extends laterally along gastric wall (B) and is engaged on gastric wall (B), after removal of the insertion tool (20).

Figure 16:
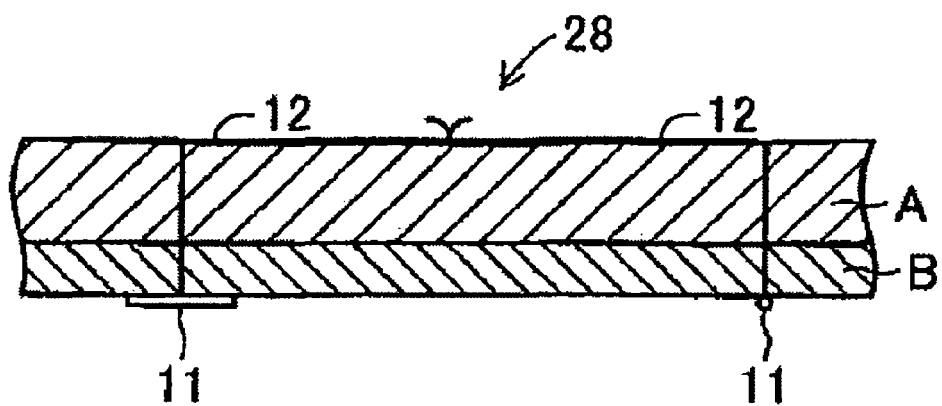
FIG. 16 is a cross section showing the gastric wall affixed to the abdominal wall by the locking part.
Figure 17:
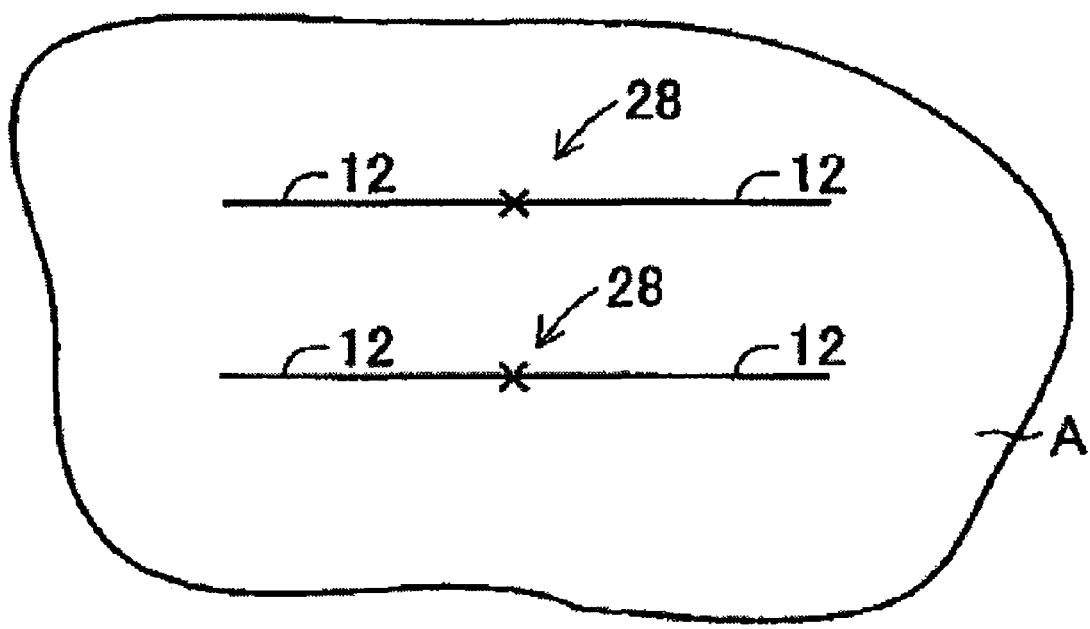
FIG. 17 is a plan view showing two sutured parts formed in the abdomen.

As shown in FIG. 16, more than one suture thread (12) is affixed to the body wall and internal organ to form a suture part (28). The base ends of the suture threads (12) of organopexy tools (10) extending outside of the patient's body are connected to each other, forming sutured part (28). Additional sutured parts (28) could be formed near sutured part (28) to give the state shown in FIG. 17. A novel technique for making multiple sutures is disclosed in Japanese Patent Application Funamura 129213[2005]. A subsequent procedure is performed to attach a molded gastric tube or the like with gastric wall (B) affixed to abdominal wall (A) by organopexy tools (10) in this way.

Figure 18:
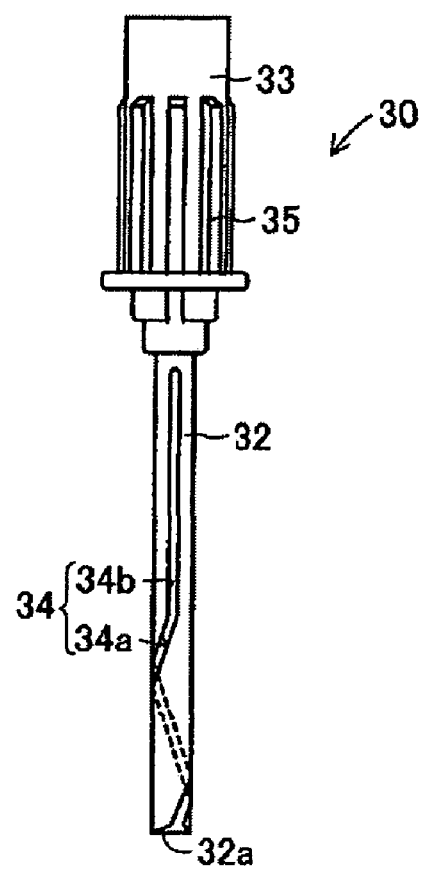
FIG. 18 is a front view showing the removal tool.
Figure 19:
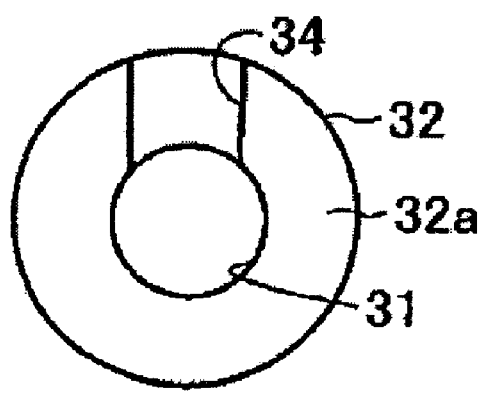
FIG. 19 is a bottom view of FIG. 18.

As shown in FIG. 18, the removal tool (30) is used to remove the organopexy tool (10). Removal tool (30) comprises a cylindrical part (32) made of stainless steel from which a hole (31) (refer to FIG. 19) is formed and grip part (33) made of resin furnished at the base end of cylindrical part (32). A notch part (34) is formed in the cylindrical part (32) from tip (32a) toward the base end passing between the outer peripheral surface and the inner peripheral surface. The portion of notch part (34) at the lower part has a spiral-shaped notch part (34a) that extends axially while encircling the periphery, and the portion toward the upper part of notch part (34) has a straight groove (34b) that extends axially. Grip part (33) is formed in a columnar shape, and an uneven part (35) to prevent slipping is formed on the peripheral surface.

Figure 20:
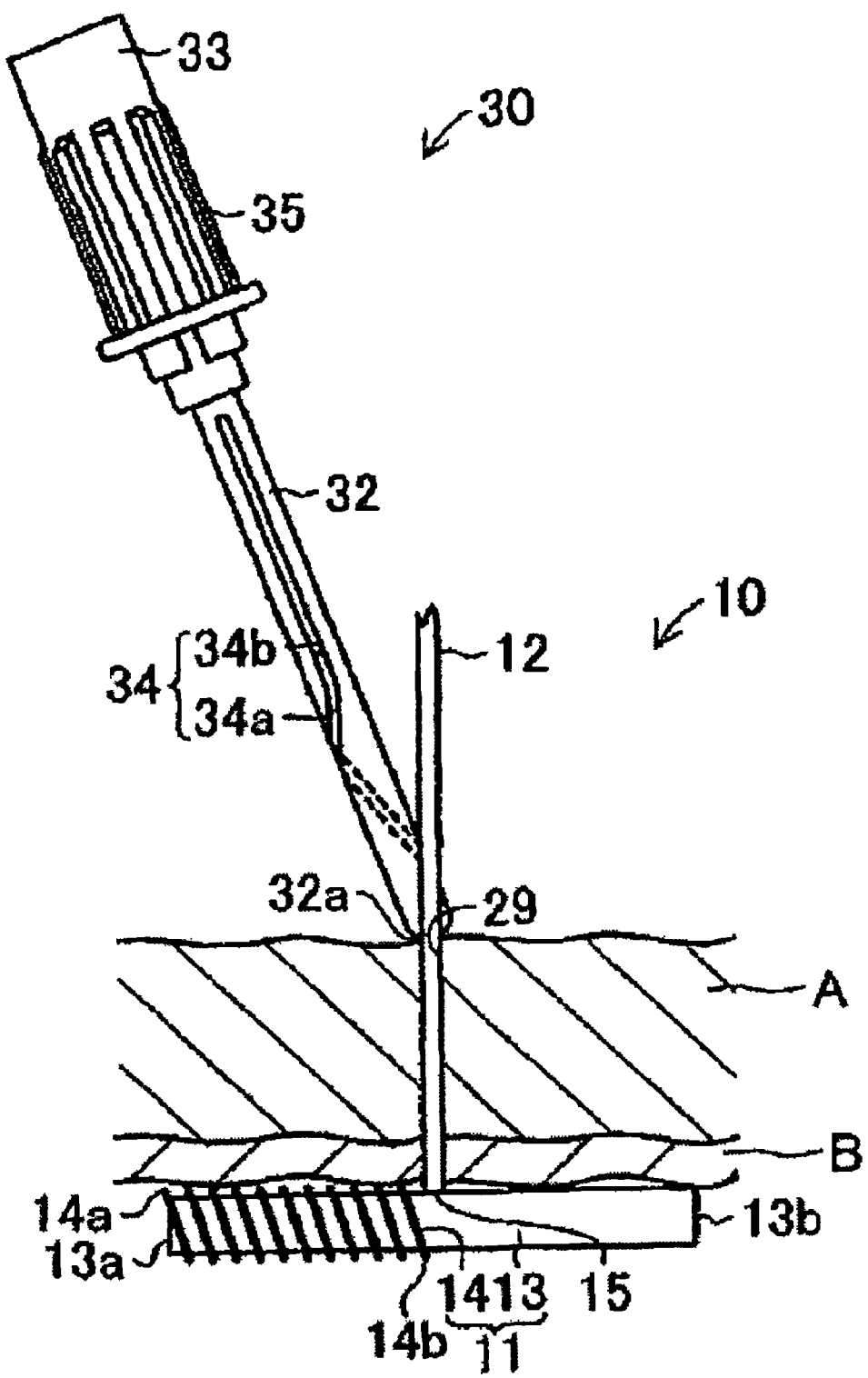
FIG. 20 is a cross section showing the removal tool following the suture thread and positioned in the hole.

FIG. 20 illustrates the removal of the organopexy tool (10) from the patient's body using the removal tool (30). The suture thread (12) previously tied is separated. The tip (32a) of cylindrical part (32) is brought into contact with the portion on the surface of abdominal wall (A) where suture thread (12) protrudes, and the lower end of notch part (34) is brought into contact with suture thread (12). The suture thread (12) is caught inside notch part (34), and cylindrical part (32) is inserted into hole (29) formed in abdominal wall (A) and gastric wall (B), with the suture thread (12) enters notch part (34) to be wrapped on the outer peripheral surface of cylindrical part (32) of removal tool (30).

Figure 21:
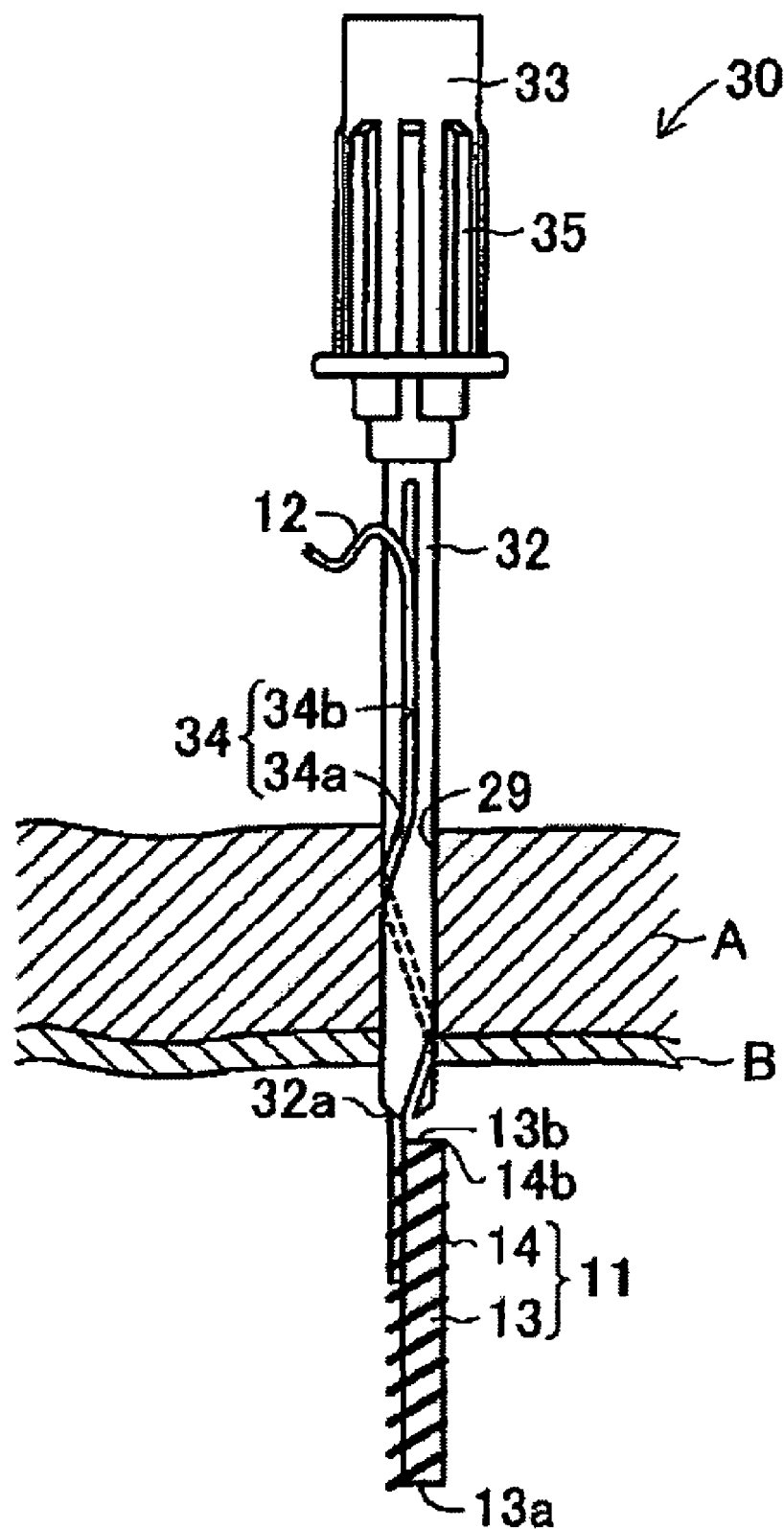
FIG. 21 is a cross section showing the locking part and the suture thread in a straight line.

Referring to FIG. 21, the tip (32a) of cylindrical part (32) is brought into contact with locking part (11), and the removal part (30) is pushed though hole (29). A part of the base end of suture thread (12) protruding outside the patient's body enters cylindrical part (32) with locking part (11) positioned on the inward side of gastric wall (B), and the tension on suture thread (12) is loosened. After loosening the suture thread (12), the force compressing coil spring (14) is released, and coil spring (14) extends as shown in FIG. 21. Because of this, the portion at the tip of suture thread (12) will follow the portion at the other end (13b) of rod-shaped part (13), and locking part (11) and suture thread (12) are extended in a straight line. In this case, the upper end of locking part (11), (other end (13b) of rod-shaped part (13)) will be positioned below tip (32a) of cylindrical part (32). In this state, the base end of suture thread (12) is slowly pulled through the cylinder part (32) of the removal tool (30).

Figure 22:
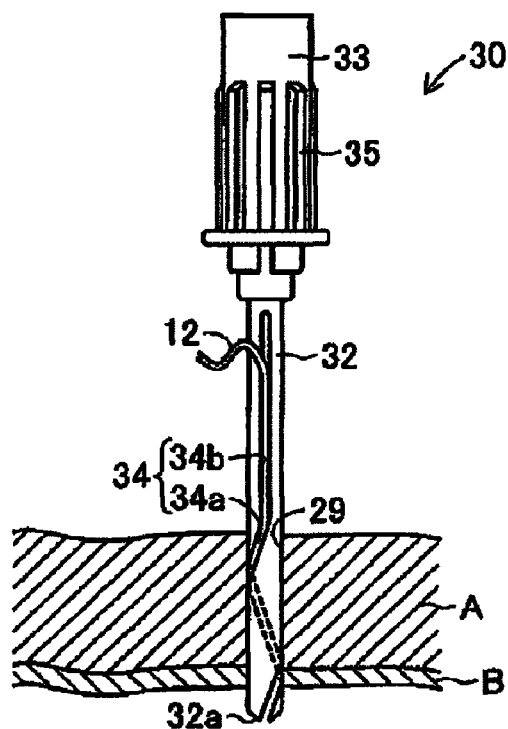
FIG. 22 is a cross section showing the locking part put inside the removal tool.

As shown in FIG. 22, locking part (11) is removed through cylindrical part (32). The removal tool (30) is pulled at the point where locking part (11) is inside cylindrical part (32) and then pulled out of the patient's body. The operation to remove organopexy tools (10) is completed by removing the other organopexy tools (10) from the patient's body in the same way. In this embodiment, the organopexy tool set according to the present invention comprises an organopexy tool (10) and insertion tool (20) or an organopexy tool (10) and removal tool (30).

As shown in FIG. 2, the organopexy tool (10) comprises a rod-shaped locking part (11) and a suture thread (12) connected to locking part (11). Locking part (11) comprise a rod-shaped part (13) and coil spring (14). One end (14a) of the coil spring (14) is affixed to one end (13a) of rod-shaped part (13) and covering the outer peripheral surface of rod-shaped part (13). The end of suture thread (12) is connected to the approximate middle part of, in the lengthwise orientation, rod-shaped part (13) through the inward side of coil spring (14) from the other end (13b) of rod-shaped part (13).

Figure 13:
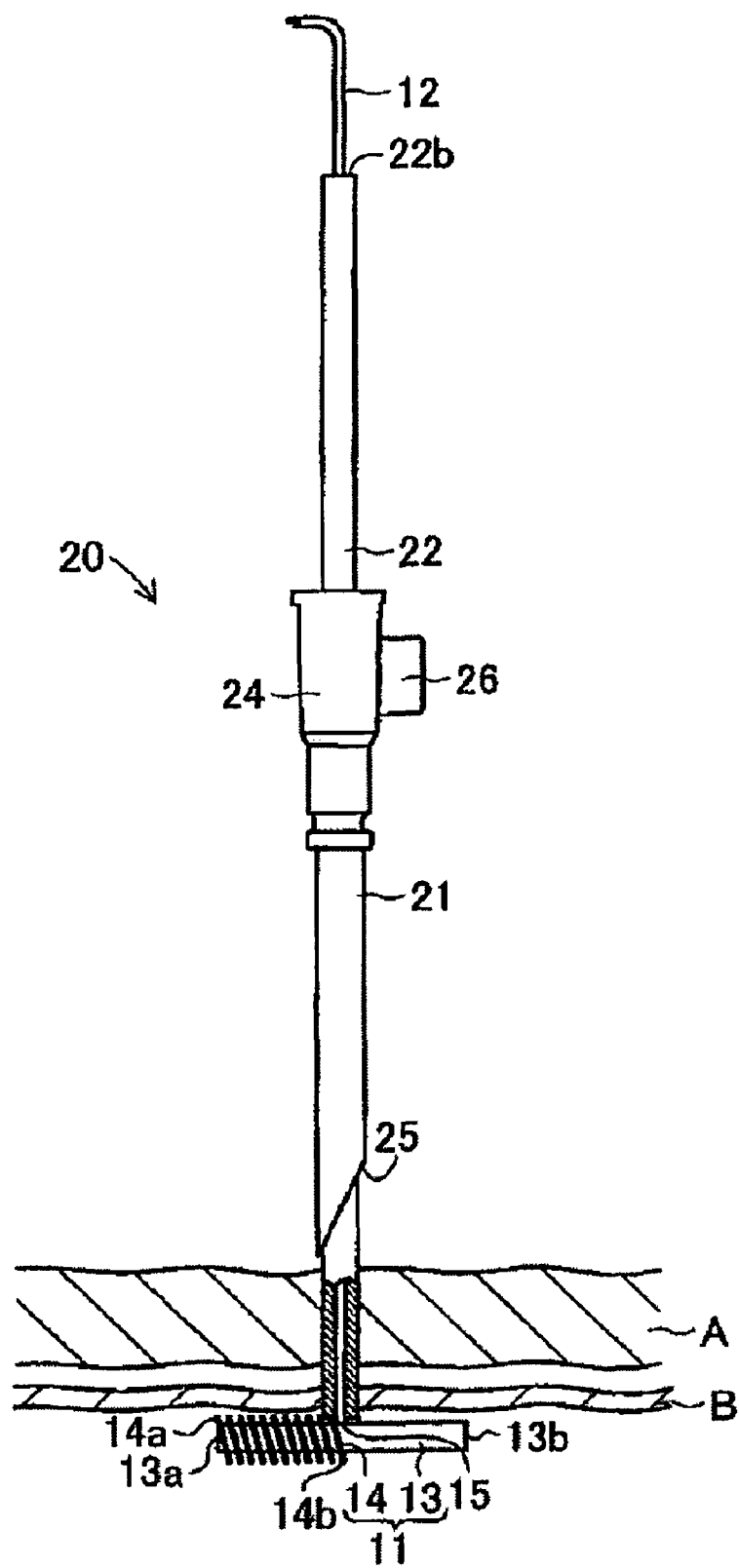
FIG. 13 is a partial cutaway cross section showing the insertion tool retracted causing the locking part to touch the gastric wall.

As shown in FIG. 13, the locking part (11) is locked on the inward side of gastric wall (B) and suture thread (12) is pulled, causing the locking part (11) and suture thread (12) to form a T shape, and the portion at the end of suture thread (12) protrudes outside the patient's body. As shown in FIG. 16, a sutured part (28) is formed by attaching two organopexy tools (10) at prescribed positions on the abdomen and connecting the suture threads (12) protruding outside the body together resulting in the gastric wall (B) being affixed to the abdominal wall (A).

Referring to FIG. 5, the insertion tool (20) comprises a puncture needle (21) for insertion that houses a locking part

(11) and the tip (25) of which is formed to be sharp, and a tubular push-out part (22) that is suitable to push locking part (11) inside the puncture needle (21) for insertion out of the open tip of puncture needle (21). Therefore, by inserting puncture needle (21) for insertion into the patient's body with locking part (11) housed in puncture needle (21) and pushing tubular push-out part (22) into the puncture needle for insertion (21), locking part (11) is suitable to be pushed out inside gastric wall (B) smoothly.

Figure 14:
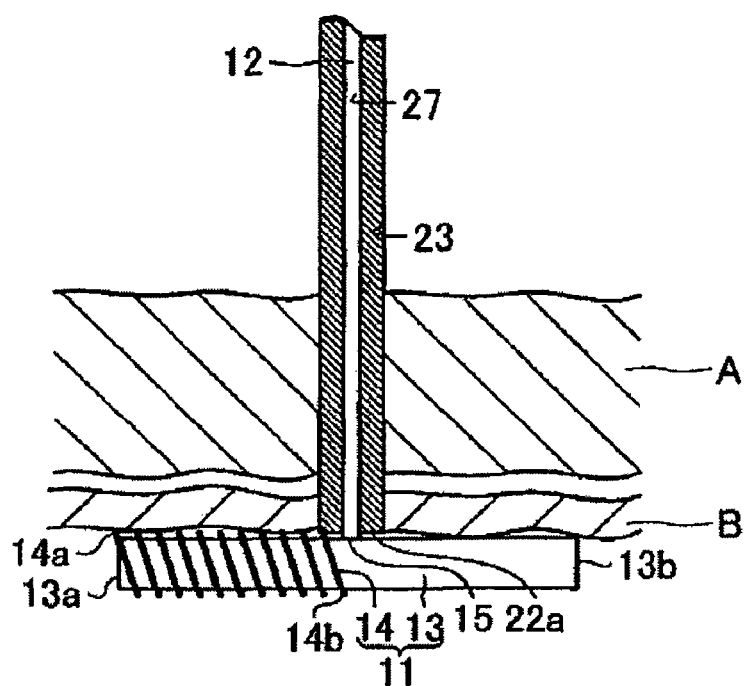
FIG. 14 is a cross section showing the major parts in FIG. 13 enlarged.

Referring to FIG. 14, the organopexy tool (10) is removed from the patient's body using the removal tool (30). The locking part (11) disposed on the inner wall of gastric wall (B) is pushed by removal tool (30) and moved toward the inside of the gastric wall (B). The suture thread (12) is loosened when the locking part (11) is pushed by the removal tool (30), the coil spring (14) extends and locking part (11) and suture thread (12) form a straight line. By pulling suture thread (12) in this state, locking part (11) can enter cylindrical part (32) of removal tool (30), and locking part (11) is suitable to be removed from the body along with removal tool (30).

Figure 25:
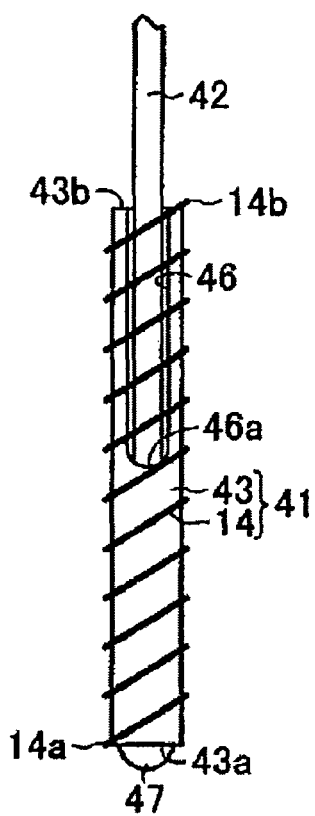
FIG. 25 is a front view showing the organopexy tool when the locking part and the suture thread are extended in a straight line and removed.
Figure 26:
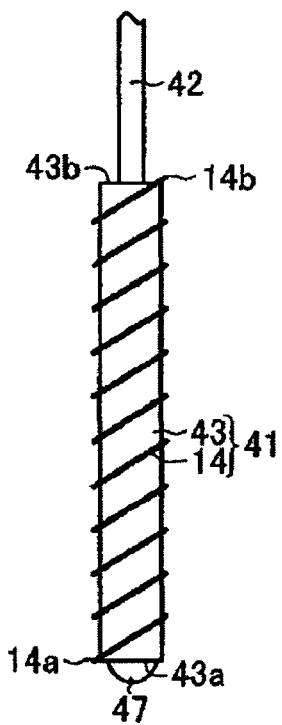
FIG. 26 is a side view of FIG. 25.
Figure 27:
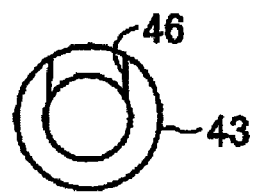
FIG. 27 is a side view showing the rod-shaped part with which the organopexy tool shown in FIG. 23 is provided.

FIGS. 23-26 show an organopexy tool (40) in a second embodiment of the present invention. With organopexy tool (40), rod-shaped part (43) comprises a locking part (41), as shown in FIG. 27, and a notch part (46) that comprises a tube body in which a hole (not shown) is formed in the middle that passes between the inner circumference and the outer circumference of rod-shaped part (43). The hole is formed between the middle part axially and the other end (43b). An engaging sphere (47) is the engaging part of the present invention and is connected to the end of suture thread (42). Engaging sphere (47) is sized such that it is suitable to engage in the open edge of one end (43a) of rod-shaped part (43). Suture thread (42) also extends outside from end (46a) of notch part (46) through the inside of the portion at one end (43a) of rod-shaped part (43) from the engaging sphere (47). The start of the exposed part in the present invention is constituted by end (46a).

Figure 23:
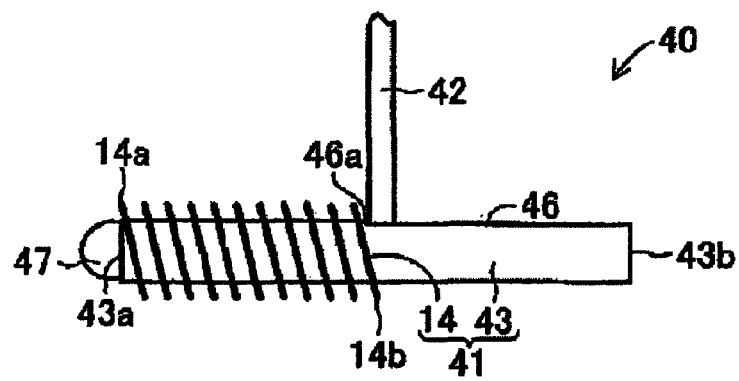
FIG. 23 is a front view showing an organopexy tool pertaining to a second embodiment of the present invention when affixed.
Figure 24:
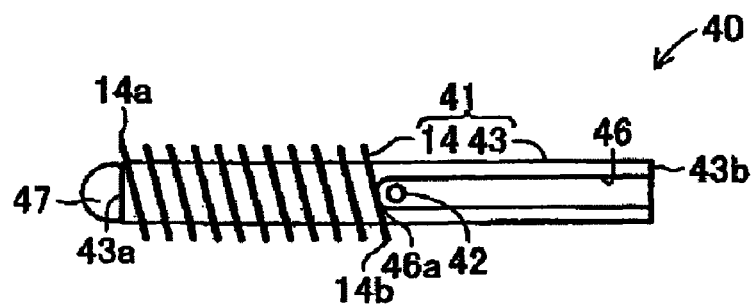
FIG. 24 is a plan view of FIG. 23.

The other parts of organopexy tool (40) are the same as organopexy tool (10) in the first embodiment as described above. Therefore, the same symbols are assigned to the same parts, and explanations are omitted. As shown in FIGS. 25 and 26, the suture thread (42) is positioned in the middle inside rod-shaped part (43) so coil spring (14) will not become tangled. By pulling suture thread (42) toward the outside of notch part (46), the organopexy tool (40) is suitable to be put into the T position as shown in FIGS. 23 and 24. The remaining use and structure of organopexy tool (40) is the same as with organopexy tool (10) described above.

Figure 28:
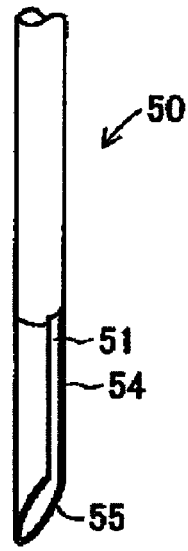
FIG. 28 is an oblique view showing an insertion tool used with an organopexy tool set pertaining to the second embodiment.

FIG. 28 shows insertion tool (50) used with an organopexy tool set provided with organopexy tool (40). Insertion tool (50) comprises a tube body inside of which a hole (51) is provided, and the tip (55) is cut in a direction diagonal to the axial orientation to form a point. A notch part (54) is formed perfectly straight toward the upper end of insertion tool (50) from the open upper end of tip (55). When organopexy tool (40) is attached to a patient's body using insertion tool (50), the locking part (41) enters the notch part (54) from tip (55) of insertion tool (50) with suture thread (42) sticking outside.

Referring to FIGS. 26 and 28, after insertion tool (50) punctures the patient's body, rod-shaped part (43) is pushed out by a pressing part (not shown) from hole (51) in the insertion tool (50). The organopexy tool (40) is attached by pulling insertion tool (50) out of the patient's body. The locking part (41) slips out of tip (55) of insertion tool (50) and remains in gastric wall (B). The suture thread (42) that is sticking out of the patient's body is passed into the bore of tubular pressing part (22), and tubular pressing part (22) is inserted into the patient's body. By pulling suture thread (42), locking part (41) is pulled toward notch part (54) and inclines in a direction perpendicular to suture thread (42).

Figure 29:
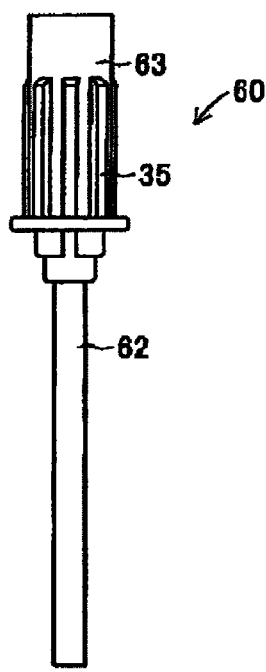
FIG. 29 is a front view showing a removal tool used with the organopexy tool set pertaining to the second embodiment.

Referring to FIG. 29, a removal tool (60) used with an organopexy tool set is provided with the organopexy tool (40). The removal tool (60) has a cylindrical part (62) with no notch part. The inside of cylindrical part (62) connects to the upper end of grip part (63), and the upper end of grip part (63) is open. The other parts of removal tool (60) are the same as for removal tool (30) described above. Therefore, the same symbols denote the same parts, and explanations are omitted. Because of this, the structure of removal tool (60) will be simple, and its manufacture will be easy. When organopexy tool (40) is removed, the same operation as the aforementioned operation is used with suture thread (42) passed toward the upper end of grip part (63) from the tip (32a) of cylindrical part (62). Removal of organopexy tool (40) will also be easy and reliable because of this. Otherwise, the operation and effects of removal tool (60) are the same as for removal tool (30) described above.

The organopexy tool and organopexy tool set pertaining to the present invention are not limited to the embodiments described above and can be implemented with appropriate changes. For example, with the aforementioned first embodiment, the organopexy tool set comprises an organopexy tool (10), insertion tool (20) and removal tool (30), and with the second embodiment, the organopexy tool set comprises an organopexy tool (40), insertion tool (50) and removal tool (60), but these combinations can be changed as is appropriate. Also, with the embodiments described above, suture threads (12) and (42) that constitute organopexy tools (10) and (40) were made with nylon, but the suture threads are not limited to nylon and could be constituted with polyester, silk, polyolefin, or the like. In place of coil spring (14) of locking parts (11) and (41), a tubular elastic member or the like can be used, as long as it can be made to contract by pulling suture threads (12) and (42) against locking parts (11) and (41).

In addition, tips (25) and (55) of insertion tools (20) and (50) were sharp, but the insertion tool can be made with a tube whose tip is not sharp. The outer peripheral surface of tip (22a) of tubular push-out part (22) can be formed so as to gradually narrow down. With this, coil spring (14) is made to contract by tip (22a) of tubular push-out part (22) so that the space between suture thread (12) and the other tip (13b) of rod-shaped part (13) is forced open, and the operation to put locking part (11) and suture thread (12) in a T shape will be more reliable. Removal tool (60) shown on FIG. 29 could also be constituted with just cylindrical part (62) by omitting grip part (63).

In addition, the shape, materials or other constitution of the insertion and removal tools could also be changed as is appropriate. For example, as the material constituting insertion tools (20) and (50), nitinol, titanium or the like can be used rather than stainless steel. As the material constituting removal tools (30) and (60), nitinol, titanium or another metal material, or polycarbonate, nylon, fluororesin or another resin material can be used, rather than stainless steel. In addition, the organopexy tool and the organopexy tool set pertaining to the present invention are not limited to suturing abdominal wall (A) and gastric wall (B), but can also be used for suturing body walls and organs at other places in the body, e.g., the kidneys or the bladder.

Other variations and modifications will be recognized by those of ordinary skill in the art as being within the scope of the present invention.

The invention claimed is:

1. An organopexy tool comprising a locking part and a suture thread connected to the locking part, the locking part including a rod-shaped part and an elastic telescoping member positioned about the rod shaped part, the suture thread having a first end connected to a middle part, in the axial direction, of the rod-shaped part and extending axially along the rod-shaped part within the telescoping member such that a second end of the suture thread extends externally of the telescoping member and wherein when the second end of the suture thread is pulled away from the rod-shaped part, the elastic telescoping member is engaged by the suture thread and contracts such that a first end of the elastic telescoping member is positioned at the middle part of the rod shaped part and the suture thread and rod-shaped part form a T shape.

2. The organopexy tool described in claim 1, wherein a second end of the elastic telescoping member is affixed to one end of the rod-shaped part such that the elastic telescoping member is positioned about an outer peripheral surface of the rod-shaped part.

3. The organopexy tool described in claim 2 wherein an engaging part is fixed to the end part of the suture thread, and further wherein the engaging part is engaged in an open end of the rod-shaped part, the suture extending through the rod-shaped member and the notch part to a position externally of the rod-shaped part.

4. The organopexy tool described in claim 1, wherein the rod-shaped part comprises a cylindrical body and a notch part through which the suture thread can pass and wherein the suture thread is passed through the outer peripheral surface from the inner peripheral surface of the cylindrical body.

5. An organopexy tool set comprising the organopexy tool described in of claim 1 and further including an insertion tool dimensioned to house the organopexy tool therein.

6. The organopexy tool set described in claim 5, wherein the insertion tool comprises a single puncture needle for insertion into a patient, the puncture needle being dimensioned to house the locking part of the organopexy tool, the insertion tool further including, a tubular push-out part that is positioned within the puncture needle for insertion with the suture thread and wherein the locking part of the organopexy tool is positioned to be pushed out from an opening at a tip of the puncture needle.

7. The organopexy tool set described in claim 5, wherein the elastic telescoping member is a coil spring.

8. An organopexy tool set comprising the organopexy tool described in claim 1 and further including a removal tool configured to remove the organopexy tool from an organ, wherein the removal tool comprises a tubular body dimensioned to receive the suture thread and the locking part.

9. The organopexy tool set described in claim 8, wherein the removal tool comprises a cylindrical part and a grip part furnished at a base end of the cylindrical part, and wherein a spiral-shaped notch part extends axially along the periphery of the cylindrical part from the tip of the cylindrical part toward the base end portion of the cylindrical part, the notch part passing between an outer peripheral surface and an inner peripheral surface of the cylindrical part.

* * * * *